(12) United States Patent
Baxter et al.

(10) Patent No.: US 6,887,876 B2
(45) Date of Patent: May 3, 2005

(54) BENZAMIDINE DERIVATIVES

(75) Inventors: Ellen W. Baxter, Glenside, PA (US); Samuel O. Nortey, Elkins Park, PA (US); Allen B. Reitz, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 201 days.

(21) Appl. No.: 10/014,081

(22) Filed: Dec. 11, 2001

(65) Prior Publication Data

US 2002/0123489 A1 Sep. 5, 2002

Related U.S. Application Data

(60) Provisional application No. 60/255,658, filed on Dec. 14, 2000.

(51) Int. Cl.[7] ............... A61K 31/495; A61K 31/496; C07D 295/125; C07D 409/12
(52) U.S. Cl. .................. 514/252.12; 514/252.14; 514/255.03; 514/218; 544/379; 544/393; 544/394; 544/399; 544/400; 540/575
(58) Field of Search ............... 544/379, 393–394, 544/399–400; 514/252.12, 252.14, 255.03

(56) References Cited

U.S. PATENT DOCUMENTS

| | | |
|---|---|---|
| 3,793,322 A | 2/1974 | Shroff et al. |
| 3,962,248 A | 6/1976 | Schneider |

FOREIGN PATENT DOCUMENTS

| | | |
|---|---|---|
| WO | WO 93/15062 A1 | 8/1993 |
| WO | WO 97/23466 A1 | 7/1997 |
| WO | WO 98/28270 A1 | 7/1998 |
| WO | WO 98/28275 A1 | 7/1998 |
| WO | WO 99/33806 A1 | 7/1999 |

OTHER PUBLICATIONS

Snyder et al. Trends in Pharmacological Sciences vol. 24, No. 4, p. 198–205 (2003).*

James B. Thomas, Robert N. Atkinson et al 4–[(8–Alkyl–8–azabicycio[3.2.1] octyl)–3–octyl–3–yl)–3–arylanilino]–N,N–diethylbenzamides: High Affinity Selective Ligands for the Delta Opioid Receptor Illustate Factors Important to Antagonist Activity Bioorganic & Medicinal Chemistry Letters: 10(2000) 1281–1284.

Robert E. Boyd et al., Synthesis and Binding Affinities of 4–Diarylaminotropanes, a New Class of Delta Opiod Agonists, Bioorganic & Medicinal Chemistry Letters 10 (2000) 1109–1111.

Peter J Munson et al; Ligand: A Versatile Computerized Approach for Characterization of Ligand–binding Systems, Analytical Biochemistry, 107, 220–239 (1980).

H.O. J. Collier, et al., The Abdominal Constriction Response and its Suppression By Analgesic Drugs in The Mouse, Br. J. Pharmac. Chemother, (1968), 32, 295–310.

Gutkowska, B., et al., Acta Pol. Pharm., 1984, 41(6), 613–617.

Nortey et al, Bioorganic & Medicinal Chemistry Letters 11, p. 1741–1743 (2001).

PCT International Search Report, dated Jun. 18, 2002 for PCT Int. Appl. No. PCT/US01/47894. filed Dec. 12, 2001, which is related to U.S. Appl. No. 10/014,081, filed Dec. 11, 2001.

\* cited by examiner

*Primary Examiner*—Emily Bernhardt

(57) ABSTRACT

Benzamidine derivatives

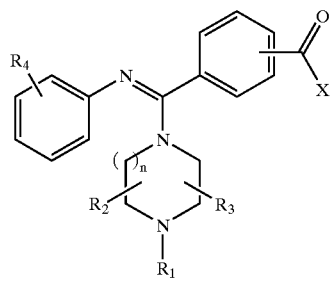

are useful delta-opioid receptor modulators, agonists useful as analgesics and antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases.

15 Claims, No Drawings

BENZAMIDINE DERIVATIVES

This application claims the benefit of U.S. Ser. No. 60/255,658, a provisional application, filed on Dec. 14, 2000, which is hereby incorporated by reference in its entirety.

FIELD OF THE INVENTION

The present invention is directed to delta-opioid receptor modulators and methods for use thereof. More particularly, the present invention is directed to benzamidine derivatives which are delta-opioid receptor agonists or antagonists and methods for use thereof.

BACKGROUND OF THE INVENTION

WO 97/23466 describes compounds as having an analgesic effect of a general and one preferred formula:

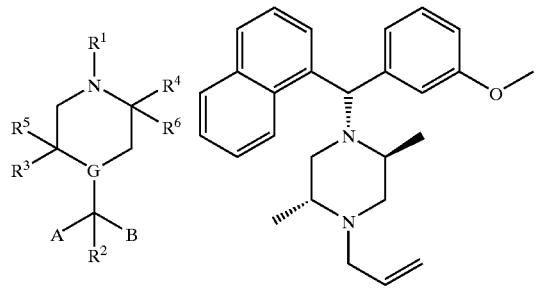

WO 98/28270 describes compounds as having an analgesic effect of a general and one preferred formula:

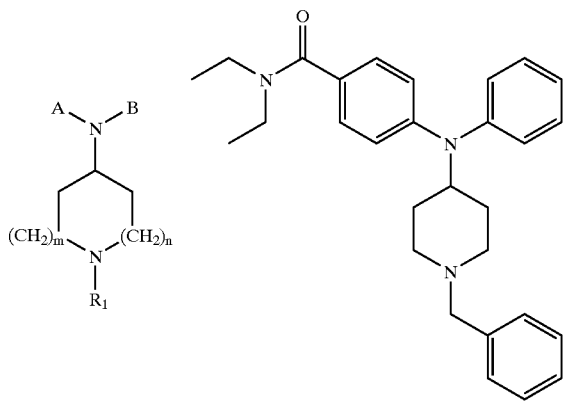

WO 98/28275 describes compounds as having an analgesic effect of a general and one preferred formula:

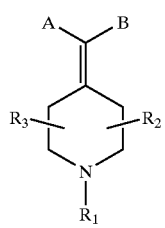

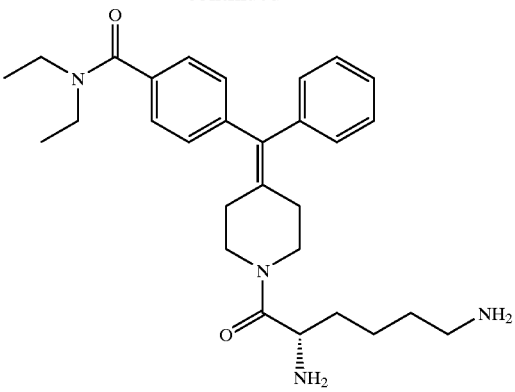

Amide derivatives of 3-aminotropane have been prepared and described as having potential pharmacological activity, Gutkowska, B., et al., *Acta Pol. Pharm.*, 1984, 41(6), 613–617, of the formula:

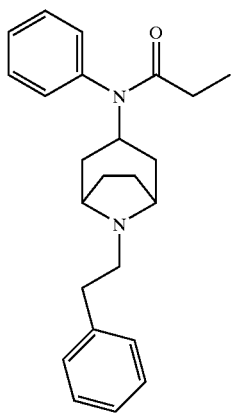

WO 93/15062 describes compounds as delta-opioid (δ-opioid) and mu-opioid (μ-opioid) receptor agonists of (approximately) the general formula:

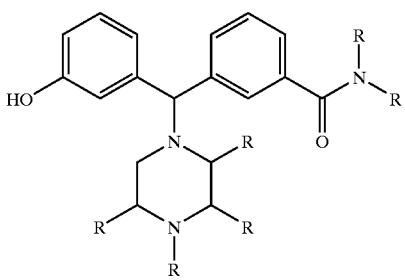

The foregoing reference compounds have been described as either δ-opioid or μ-opioid receptor agonists or antagonists.

U.S. Pat. No. 3,793,322 describes compounds of the general formula:

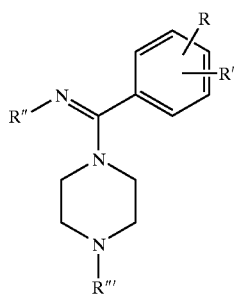

wherein R and R' are hydrogen, lower alkyl, hydroxy, lower alkoxy, halogen or trifluoromethyl and may be the same or different; R" is lower alkyl, lower alkenyl, cycloalkyl, or phenyl, and R'" is hydrogen, lower alkyl, lower alkenyl, carboalkoxy, carboalkoxyalkyl, formyl, phenyl, halophenyl, cinnamyl, benzyl or benzhydryl as having hypoglycemic activity. The lower alkyl, lower alkoxy and lower alkenyl groups may be branched or straight chained and contain up to 6 carbon atoms. The cycloalkyl groups contain from 3 to 7 carbon atoms in the ring which may also carry a lower alkyl substituent. The carboalkoxy groups contain alkyl groups having from 1 to 5 carbon atoms and include carbomethoxy, carbethoxy, carbopropoxy, carbobutoxy and the like. Desirably, R and R' are lower alkyl, preferably methyl, or halogen, preferably chloro; R may be hydrogen and R' is then chloro, lower alkyl, preferably methyl, or trifluoromethyl; R" is lower alkyl, preferably isobutyl, and R'" is carbethoxy. Exemplified compounds include those wherein R is selected from hydrogen, chlorine, fluorine or methyl; R' is selected from hydrogen, chlorine, fluorine, methyl, methoxy, hydroxy or trifluoromethyl; R" is selected from hydrogen, chlorine, fluorine, methyl, ethyl, n-propyl, n-butyl, i-butyl, i-amyl, n-hexyl, allyl, cyclohexyl, phenyl or 3,4-dimethylphenyl; R'" is selected from hydrogen, methyl, ethyl, n-hexyl, allyl, phenyl, 4-Cl-phenyl, benzhydryl, benzyl, 2,4-Cl$_2$-benzyl, 2,3,4-(MeO)$_3$-benzyl, COOEt or CHO.

U.S. Pat. No. 3,962,248 describes compounds of the formula:

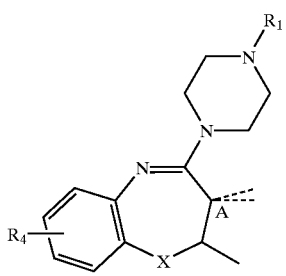

wherein A signifies the structure

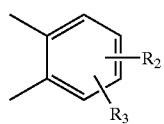

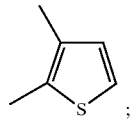

$R_1$ is hydrogen, alkoxyalkyl of 2 to 6 carbon atoms in the aggregate thereof, alkyl of 1 to 4 carbon atoms, hydroxyalkyl of 1 to 4 carbon atoms or acyloxyalkyl of 3 to 22 carbon atoms in the aggregate thereof, $R_4$ is hydrogen, alkyl, alkoxy or alkylthio, wherein the alkyl groups have 1 to 4 carbon atoms, halogen or trifluoromethyl; when A denotes Z1, X is a —CH$_2$—, —O—, —S—, —NH or —N-alkyl group wherein the alkyl group has 1 to 3 carbon atoms, $R_2$ is hydrogen, dialkylamino-sulphonyl, alkyl-sulphonyl, wherein the alkyl groups have 1 to 4 carbon atoms, alkoxy or alkylthio of 1 to 4 carbon atoms, halogen, nitro, trifluoromethylsulphonyl, trifluoromethoxy, trifluoromethylthio, acetyl, cyano or trifluoromethyl, and $R_3$ is hydrogen, halogen or alkyl of 1 to 4 carbon atoms, or when A denotes Z2, X is a —CH$_2$— or —S— group as having neuroleptic activity.

The synthesis and binding affinities for 4-Diarylaminotropane compounds of the general formula:

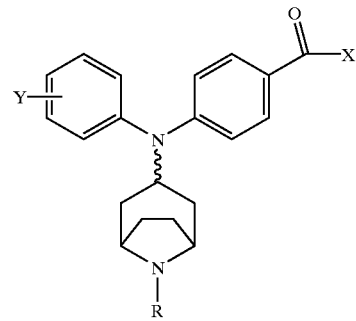

wherein R is hydrogen, methyl, propyl, hexyl, 2-ethylbutyl, allyl, 3,3-dimethallyl, cyclohexylmethyl, phenethyl, phenylpropyl, 2,2-diphenylethyl, 3,4-dimethoxyphenethyl, 4-fluorophenethyl, 2-furylmethyl; 3,4-methylenedioxybenzyl, cyano and X is N,N-dimethylamino, N,N-diethylamino, N,N-dipropylamino, N-methyl, N-ethylamino, N-methyl, N-propylamino, N-methyl, N-phenylamino, N-ethyl, N-(4-methyl)benzylamino, N-butyl, N-ethylamino, N-butyl, N-propylamino, [N-ethyl, N-(2-methyl)allyl]amino, hydroxy, O-t-butyl and 1-pyrrolidinyl; and, Y is hydrogen, methoxy and methylthio as δ-opioid agonists have been described (Boyd, R. E., Carson, J. R., Codd, E. E., Gauthier, A. D., Neilson, L. A and Zhang, S-P., *Biorg. Med. Chem. Lett.*, 2000, 10: 1109–1111). 4-[(8-Alkyl-8-azabicyclo[3.2.1]octyl-3-yl)-3-arylanilino]-N,N-diethylbenzamides have also been described as selective δ-opioid ligands (Thomas, J. B., Atkinson, R. N., Rothman, R. B., Burgess, J. P., Mascarella, S. W., Dersch, C. M., Xu, H. and Carroll, F. I., *Biorg. Med. Chem. Lett.*, 2000, 10: 1281–1284).

The benzamidine derivatives of the present invention have not been previously described as δ-opioid receptor modulators.

Accordingly, it is an object of the present invention to provide benzamidine derivatives which are δ-opioid receptor modulators. It is also an object of the present invention to provide benzamidine derivatives which are δ-opioid receptor selective agonists useful as analgesics having reduced side-effects. It is another object of the present invention to provide δ-opioid receptor antagonists useful for treating immune disorders, inflammation, neurological conditions, psychiatric conditions, drug abuse, alcohol abuse, gastritis, diarrhea, cardiovascular disorders or respiratory disorders. It is a further object of the present invention to provide a method for treating a disorder modulated by the δ-opioid receptor.

SUMMARY OF THE INVENTION

The present invention provides benzamidine derivatives of Formula (I):

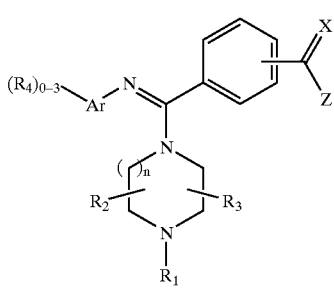

Formula I wherein:

X is a substituent selected from the group consisting of S and O;

Z is a substituent selected from the group consisting of $O(R_5)$ and $N(R_6)(R_7)$;

the moiety —C(X)Z is substituted on the phenyl at the 3 or 4 position;

n is an integer from 1 to 2;

$R_1$ is a substituent selected from the group consisting of hydrogen, $C_{1-6}$alkyl, $C_{2-6}$alkenyl, $C_{2-6}$alkynyl, $C_{1-6}$alkoxy($C_{1-6}$)alkyl, $C_{1-6}$alkoxycarbonyl, $C_{1-6}$alkyl-($C_{1-6}$)alkoxycarbonyl, formyl, aryl, aryl($C_{1-6}$)alkyl, diaryl($C_{1-6}$)alkyl and heteroaryl($C_{1-6}$)alkyl; wherein aryl and heteroaryl are optionally substituted with one to three substituents independently selected from the group consisting of halogen, $C_{1-4}$alkyl, $C_{1-4}$alkoxy, amino, $C_{1-4}$alkylamino, di($C_{1-4}$alkyl)amino, trihalo$C_{1-4}$alkyl and trihalo$C_{1-4}$alkoxy;

$R_2$ and $R_3$ are substituents independently selected from the group consisting of hydrogen and $C_{1-6}$alkyl;

Ar is aryl optionally substituted with one to three substituents selected from $R_4$;

$R_4$ is a substituent selected from the group consisting of halogen, $C_{1-6}$alkyl, $C_{1-6}$alkoxy, aryl, aryl($C_{1-6}$)alkyl, heteroaryl, heteroaryl($C_{1-6}$)alkyl, amino, $C_{1-6}$alkylamino, di($C_{1-6}$alkyl)amino, cyano, hydroxy, nitro, trihalo$C_{1-6}$ alkyl and trihalo$C_{1-4}$alkoxy; alternatively, two $R_4$ substituents may be fused together on adjacent carbon atoms to form a single fused moiety, wherein the moiety is selected from the group consisting of —(CH$_2$)$_{3-5}$— and —O(CH$_2$)$_{1-3}$O—;

$R_5$ is a substituent selected from $C_{1-6}$alkyl; and, $R_6$ and $R_7$ are substituents independently selected from the group consisting of hydrogen, $C_{1-6}$alkyl, $C_{2-6}$alkenyl, $C_{3-7}$cycloalkyl, aryl and aryl($C_{1-6}$)alkyl, wherein cycloalkyl and aryl are optionally substituted with one to three substituents independently selected from the group consisting of halogen, $C_{1-4}$alkyl, $C_{2-4}$alkenyl, $C_{1-4}$alkoxy, $C_{3-7}$cycloalkyl, trihalo$C_{1-3}$alkyl and trihalo$C_{1-3}$alkoxy; alternatively, $R_6$ and $R_7$ may be fused together to form a single fused moiety, wherein the moiety is selected from the group consisting of —(CH$_2$)$_{3-5}$— and —O(CH$_2$)$_{1-3}$ O—;

and pharmaceutically acceptable enantiomers, diastereomers and salts thereof.

DETAILED DESCRIPTION OF THE INVENTION

We have discovered that the benzamidine derivatives of the present invention are useful δ-opioid receptor modulators, particularly δ-opioid receptor agonists.

An embodiment of the present invention includes those compounds wherein preferably, X is O.

Embodiments of the present invention include compounds wherein preferably, $R_1$ is a substituent selected from the group consisting of hydrogen, $C_{1-6}$alkyl, $C_{2-6}$alkenyl, $C_{1-6}$alkoxy($C_{1-6}$)alkyl, $C_{1-6}$alkoxycarbonyl, formyl, aryl, aryl($C_{1-6}$)alkyl, diaryl($C_{1-6}$)alkyl and heteroaryl($C_{1-6}$)alkyl; wherein aryl is optionally substituted with one to three substituents independently selected from halogen and $C_{1-4}$alkoxy). More preferably, $R_1$ is a substituent selected from the group consisting of hydrogen, methyl, ethyl, n-propyl, n-butyl, n-hexyl, allyl, propenyl, cinnamyl, methoxy($C_{1-3}$)alkyl, ethoxy($C_{1-3}$)alkyl, propoxy($C_{1-3}$)alkyl, $C_{1-3}$alkoxycarbonyl, formyl, phenyl (optionally substituted with one to two substituents independently selected from halogen), benzyl (optionally substituted with one to three substituents independently selected from halogen and $C_{1-4}$alkoxy), benzhydryl, phenyl($C_{2-3}$)alkyl, furyl($C_{1-3}$) alkyl, thienyl($C_{1-3}$)alkyl, pyrrolyl($C_{1-3}$)alkyl, pyrrolinyl-($C_{1-3}$)alkyl, oxazolyl($C_{1-3}$)alkyl, thiazolyl($C_{1-3}$)alkyl, imidazolyl($C_{1-3}$)alkyl, imidazolinyl($C_{1-3}$)alkyl, pyrazolyl ($C_{1-3}$)alkyl, pyrazolinyl($C_{1-3}$)alkyl, isoxazolyl($C_{1-3}$)alkyl, isothiazolyl($C_{1-3}$)alkyl, pyridinyl($C_{1-3}$)alkyl, pyridazinyl ($C_{1-3}$)alkyl, pyrimidinyl($C_{1-3}$)alkyl and pyrazinyl($C_{1-3}$) alkyl. Most preferably, $R_1$ is a substituent selected from the group consisting of hydrogen, ethyl, n-propyl, allyl, methoxyethyl, phenyl, benzyl, phenethyl and 2-thienylethyl.

Embodiments of the present invention also include compounds wherein preferably, $R_2$ and $R_3$ are substituents independently selected from the group consisting of hydrogen, methyl, ethyl, n-propyl and n-butyl. More preferably, $R_2$ and $R_3$ are substituents independently selected from the group consisting of hydrogen and methyl.

Embodiments of the present invention further include compounds wherein preferably, Ar is a substituent selected from the group consisting of phenyl and naphthalenyl optionally substituted with one to three substituents selected from $R_4$. More preferably, Ar is phenyl optionally substituted with one to three substituents selected from $R_4$. Most preferably, Ar is phenyl optionally substituted with one to two substituents independently selected from $R_4$.

An embodiment of the present invention includes compounds wherein preferably, $R_4$ is a substituent selected from the group consisting of halogen, $C_{1-4}$alkoxy and trihalo$C_{1-4}$ alkyl. More preferably, $R_4$ is a substituent selected from the group consisting of chlorine, fluorine, bromine, methoxy, ethoxy, propoxy, butoxy, trifluoromethyl and trifluoroethyl. Most preferably, $R_4$ is a substituent selected from the group consisting of chlorine, fluorine, bromine, methoxy and trifluoromethyl.

An embodiment of the present invention also includes compounds wherein preferably, $R_5$ is a substituent selected from the group consisting of methyl, ethyl, n-propyl and n-butyl. More preferably, $R_5$ is methyl.

An embodiment of the present invention further includes compounds wherein preferably, $R_6$ and $R_7$ are substituents independently selected from the group consisting of hydrogen and $C_{1-6}$alkyl. More preferably, $R_6$ and $R_7$ are substituents independently selected from the group consisting of hydrogen, methyl, ethyl, n-propyl and n-butyl. Most preferably, $R_6$ and $R_7$ are substituents independently selected from the group consisting of ethyl and n-propyl.

Exemplifying the invention is a compound of Formula (I) selected from Table 1:

TABLE 1

| Cpd. | Compound Name |
|---|---|
| 1 | N,N-diethyl-4-[(4-ethyl-1-piperazinyl)(phenylimino)methyl]-benzamide; |
| 2 | N,N-diethyl-4-[(4-ethyl-1-piperazinyl)[(3-methoxyphenyl)imino]methyl]-benzamide; |
| 3 | 4-[[(3-chlorophenylimino](4-ethyl-1-piperazinyl)methyl]-N,N-diethyl-benzamide; |
| 4 | 4-[[(3-bromophenyl)imino](4-ethyl-1-piperazinyl)methyl]-N,N-diethyl-benzamide; |
| 5 | 4-[[(3-bromophenyl)imino](4-ethyl-1-piperazinyl)methyl]-N,N-dipropyl-benzamide; |
| 6 | 4-[[(2-chlorophenyl)imino](4-ethyl-1-piperazinyl)methyl]-N,N-diethyl-benzamide; |
| 7 | 4-[[(2-chlorophenyl)imino](4-ethyl-1-piperazinyl)methyl]-N,N-dipropyl-benzamide; |
| 8 | 4-[(4-ethyl-1-piperazinyl)[(3-fluorophenyl)imino]methyl]-N,N-dipropyl-benzamide; |
| 9 | N,N-diethyl-4-[(4-ethyl-1-piperazinyl)[(3-fluorophenyl)imino]methyl]-benzamide; |
| 10 | N,N-diethyl-4-[(4-ethyl-1-piperazinyl)[(2-fluorophenyl)imino]methyl]-benzamide; |
| 11 | 4-[(4-ethyl-1-piperazinyl)[(2-fluorophenyl)imino]methyl]-N,N-dipropyl-benzamide; |
| 12 | 4-[[(3,5-dichlorophenyl)imino](4-ethyl-1-piperazinyl)methyl]-N,N-dipropyl-benzamide; |
| 13 | 4-[[(3,5-dichlorophenyl)imino](4-ethyl-1-piperazinyl)methyl]-N,N-diethyl-benzamide; |
| 14 | 4-[[(3-chlorophenyl)imino](4-propyl-1-piperazinyl)methyl]-N,N-diethyl-benzamide; |
| 15 | N,N-diethyl-4-[(phenylimino)[4-(2-propenyl)-1-piperazinyl]methyl]-benzamide; |
| 16 | 4-[(E)-[(2S,5R)-2,5-dimethyl-4-(2-propenyl)piperazinyl](phenylimino)methyl]-N,N-diethyl-benzamide; |
| 17 | N,N-diethyl-4-[(phenylimino)[4-(phenylmethyl)-1-piperazinyl]methyl]-benzamide; |
| 18 | 4-[[(2-chlorophenyl)imino](4-propyl-1-piperazinyl)methyl]-N,N-diethyl-benzamide; |
| 19 | 4-[[(2-chlorophenyl)imino][4-(2-propenyl)-1-piperazinyl]methyl]-N,N-diethyl-benzamide; |
| 20 | 4-[[(2-chlorophenyl)imino][4-(phenylmethyl)-1-piperazinyl]methyl]-N,N-diethyl-benzamide; |
| 21 | 4-[[(2-chlorophenyl)imino][4-[2-(2-thienyl)ethyl]-1-piperazinyl]methyl]-N,N-diethyl-benzamide; |
| 22 | N,N-diethyl-4-[(phenylimino)[4-[2-(2-thienyl)ethyl]-1-piperazinyl]methyl]-benzamide; |
| 23 | N,N-diethyl-4-[[4-(phenylmethyl)-1-piperazinyl][[2-(trifluoromethyl)phenyl]imino]methyl]-benzamide; |
| 24 | N,N-diethyl-4-[[4-(2-phenylethyl)-1-piperazinyl][[2-(trifluoromethyl)phenyl]imino]methyl]-benzamide; |
| 25 | 4-[[(2-chlorophenyl)imino][4-(2-phenylethyl)-1-piperazinyl]methyl]-N,N-diethyl-benzamide; |
| 26 | N,N-diethyl-4-[[4-(2-methoxyethyl)-1-piperazinyl][[2-(trifluoromethyl)phenyl]imino]methyl]-benzamide; |
| 27 | 4-[[(2-chlorophenyl)imino][4-(2-methoxyethyl)-1-piperazinyl]methyl]-N,N-diethyl-benzamide; |
| 28 | 4-[[(4-chlorophenyl)imino][4-(phenylmethyl)-1-piperazinyl]methyl]-N,N-diethyl-benzamide; |
| 30 | 4-[[(3-chlorophenyl)imino](4-ethyl-1-piperazinyl)methyl]-benzoic acid methyl ester; |
| 31 | 4-[[(3-bromophenyl)imino](4-ethyl-1-piperazinyl)methyl]-benzoic acid methyl ester; |
| 32 | 4-[[(2-chlorophenyl)imino](4-ethyl-1-piperazinyl)methyl]-benzoic acid methyl ester; |
| 33 | 4-[(4-ethyl-1-piperazinyl)[(3-fluorophenyl)imino]methyl]-benzoic acid methyl ester; |

TABLE 1-continued

| Cpd. | Compound Name |
|---|---|
| 34 | 4-[[(2-chlorophenyl)imino](4-propyl-1-piperazinyl)methyl]-benzoic acid methyl ester; |
| 35 | 4-[[(2-chlorophenyl)imino](4-phenyl-1-piperazinyl)methyl]-benzoic acid methyl ester; |
| 36 | 4-[(4-ethenyl-1-piperazinyl)(phenylimino)methyl]-benzoic acid methyl ester; |
| 37 | 4-[(phenylimino)[4-(phenylmethyl)-1-piperazinyl]methyl]-benzoic acid methyl ester; |
| 38 | 4-[[(4-chlorophenyl)imino][4-(phenylmethyl)-1-piperazinyl]methyl]-benzoic acid methyl ester; |
| 39 | 4-[[(2-chlorophenyl)imino][4-(phenylmethyl)-1-piperazinyl]methyl]-benzoic acid methyl ester; |
| 40 | 4-[[(2-chlorophenyl)imino][4-(2-phenylethyl)-1-piperazinyl]methyl]-benzoic acid methyl ester; |
| 41 | 4-[[4-(2-phenylethyl)-1-piperazinyl][[2-(trifluoromethyl)phenyl]imino]methyl]-benzoic acid methyl ester; |
| 42 | 4-[(phenylimino)[4-[2-(2-thienyl)ethyl]-1-piperazinyl]methyl]-benzoic acid methyl ester; |
| 43 | 4-[[(2-chlorophenyl)imino][4-[2-(2-thienyl)ethyl]-1-piperazinyl]methyl]-benzoic acid methyl ester; |
| 44 | 4-[[4-(2-methoxyethyl)-1-piperazinyl][[2-(trifluoromethyl)phenyl]imino]methyl]-benzoic acid methyl ester; |
| 45 | 4-[[(2-chlorophenyl)imino][4-(2-methoxyethyl)-1-piperazinyl]methyl]-benzoic acid methyl ester; |
| 46 | 4-[(4-ethyl-1-piperazinyl)(phenylimino)methyl]-benzoic acid methyl ester; |
| 47 | 4-[(4-ethyl-1-piperazinyl)[(3-methoxyphenyl)imino]methyl]-benzoic acid methyl ester; |
| 48 | 4-[(4-ethyl-1-piperazinyl)[(2-methoxyphenyl)imino]methyl]-benzoic acid methyl ester; |
| 49 | 4-[[(3,5-dichlorophenyl)imino](4-ethyl-1-piperazinyl)methyl]-benzoic acid methyl ester; |
| 50 | 4-[[(3-chlorophenyl)imino](4-propyl-1-piperazinyl)methyl]-benzoic acid methyl ester; |
| 51 | 4-[(E)-[(2S,5R)-2,5-dimethyl-4-(2-propenyl)piperazinyl](phenylimino)methyl]-benzoic acid methyl ester; |
| 52 | 3-[[(2-chlorophenyl)imino][4-(2-propenyl)-1-piperazinyl]methyl]-N,N-diethyl-benzamide; |
| 53 | N,N-diethyl-3-[(phenylimino)[4-(2-propenyl)-1-piperazinyl]methyl]-benzamide; |
| 54 | 3-[[(2-chlorophenyl)imino][4-(2-propenyl)-1-piperazinyl]methyl]-benzoic acid methyl ester; |
| 55 | 3-[(phenylimino)[4-(2-propenyl)-1-piperazinyl]methyl]-benzoic acid methyl ester; |
| 56 | N,N-diethyl-4-[[hexahydro-4-(2-phenylethyl)-1H-1,4-diazepin-1-yl](phenylimino)methyl]-benzamide; |
| 57 | 4-[[(2-chlorophenyl)imino][hexahydro-4-(2-phenylethyl)-1H-1,4-diazepin-1-yl]methyl]-N,N-diethyl-benzamide; |
| 58 | 4-[[hexahydro-4-(2-phenylethyl)-1H-1,4-diazepin-1-yl](phenylimino)methyl]-benzoic acid methyl ester; or, |
| 59 | 4-[[(2-chlorophenyl)imino][hexahydro-4-(2-phenylethyl)-1H-1,4-diazepin-1-yl]methyl]-benzoic acid methyl ester; | and pharmaceutically acceptable enantiomers, diastereomers and salts thereof.

Representative Chemical Abstracts Service (CAS) Index-like names for the compounds of the present invention were derived using the ACD/LABS SOFTWARE™ Index Name Pro Version 4.0 nomenclature software program provided by Advanced Chemistry Development, Inc., Toronto, Ontario, Canada.

In another view, exemplified benzamidine derivatives of the present invention include those compounds shown in Table 2 having the formula:

TABLE 2 wherein n, $R_1$, $R_2$, $R_3$, $R_4$ and X are selected from:

| Cpd | n | $R_1$ | $R_2$ | $R_3$ | $R_4$ | —C(O)X |
|---|---|---|---|---|---|---|
| 1 | 1 | Et | H | H | — | -4-C(O)N(Et)$_2$; |
| 2 | 1 | Et | H | H | 3-MeO | -4-C(O)N(Et)$_2$; |
| 3 | 1 | Et | H | H | 3-Cl | -4-C(O)N(Et)$_2$; |
| 4 | 1 | Et | H | H | 3-Br | -4-C(O)N(Et)$_2$; |
| 5 | 1 | Et | H | H | 3-Br | -4-C(O)N(Pr)$_2$; |
| 6 | 1 | Et | H | H | 2-Cl | -4-C(O)N(Et)$_2$; |
| 7 | 1 | Et | H | H | 2-Cl | -4-C(O)N(Pr)$_2$; |
| 8 | 1 | Et | H | H | 3-F | -4-C(O)N(Pr)$_2$; |
| 9 | 1 | Et | H | H | 3-F | -4-C(O)N(Et)$_2$; |
| 10 | 1 | Et | H | H | 2-F | -4-C(O)N(Et)$_2$; |
| 11 | 1 | Et | H | H | 2-F | -4-C(O)N(Pr)$_2$; |
| 12 | 1 | Et | H | H | 3,5-Cl$_2$ | -4-C(O)N(Pr)$_2$; |
| 13 | 1 | Et | H | H | 3,5-Cl$_2$ | -4-C(O)N(Et)$_2$; |
| 14 | 1 | Pr | H | H | 3-Cl | -4-C(O)N(Et)$_2$; |
| 15 | 1 | Allyl | H | H | — | -4-C(O)N(Et)$_2$; |
| 16 | 1 | Allyl | 2-Me | 5-Me | — | -4-C(O)N(Et)$_2$; |
| 17 | 1 | Benzyl | H | H | — | -4-C(O)N(Et)$_2$; |
| 18 | 1 | Allyl | H | H | 3-Cl | -4-C(O)N(Et)$_2$; |
| 19 | 1 | Allyl | H | H | 2-Cl | -4-C(O)N(Et)$_2$; |
| 20 | 1 | Benzyl | H | H | 2-Cl | -4-C(O)N(Et)$_2$; |
| 21 | 1 | 2-(2-thienyl)ethyl | H | H | 2-Cl | -4-C(O)N(Et)$_2$; |
| 22 | 1 | 2-(2-thienyl)ethyl | H | H | — | -4-C(O)N(Et)$_2$; |
| 23 | 1 | Benzyl | H | H | 2-CF$_3$ | -4-C(O)N(Et)$_2$; |
| 24 | 1 | Phenethyl | H | H | 2-CF$_3$ | -4-C(O)N(Et)$_2$; |
| 25 | 1 | Phenethyl | H | H | 2-Cl | -4-C(O)N(Et)$_2$; |
| 26 | 1 | 2-(methoxy)ethyl | H | H | 2-CF$_3$ | -4-C(O)N(Et)$_2$; |
| 27 | 1 | 2-(methoxy)ethyl | H | H | 2-Cl | -4-C(O)N(Et)$_2$; |
| 28 | 1 | Benzyl | H | H | 4-Cl | -4-C(O)N(Et)$_2$; |
| 29 | 1 | Et | H | H | 3-Cl | -4-C(O)OMe; |
| 30 | 1 | Et | H | H | 3-Br | -4-C(O)OMe; |
| 31 | 1 | Et | H | H | 2-Cl | -4-C(O)OMe; |
| 32 | 1 | Et | H | H | 3-F | -4-C(O)OMe; |
| 33 | 1 | Et | H | H | 2-F | -4-C(O)OMe; |
| 34 | 1 | Pr | H | H | 2-Cl | -4-C(O)OMe; |
| 35 | 1 | Ph | H | H | 2-Cl | -4-C(O)OMe; |
| 36 | 1 | Allyl | H | H | — | -4-C(O)OMe; |
| 37 | 1 | Benzyl | H | H | — | -4-C(O)OMe; |
| 38 | 1 | Benzyl | H | H | 4-Cl | -4-C(O)OMe; |
| 39 | 1 | Benzyl | H | H | 2-Cl | -4-C(O)OMe; |
| 40 | 1 | Phenethyl | H | H | 2-Cl | -4-C(O)OMe; |
| 41 | 1 | Phenethyl | H | H | 2-CF$_3$ | -4-C(O)OMe; |
| 42 | 1 | 2-(2-thienyl)ethyl | H | H | — | -4-C(O)OMe; |
| 43 | 1 | 2-(2-thienyl)ethyl | H | H | 2-Cl | -4-C(O)OMe; |
| 44 | 1 | 2-(methoxy)ethyl | H | H | 2-CF$_3$ | -4-C(O)OMe; |
| 45 | 1 | 2-(methoxy)ethyl | H | H | 2-Cl | -4-C(O)OMe; |
| 46 | 1 | Et | H | H | — | -4-C(O)OMe; |
| 47 | 1 | Et | H | H | 3-MeO | -4-C(O)OMe; |
| 48 | 1 | Et | H | H | 2-MeO | -4-C(O)OMe; |
| 49 | 1 | Et | H | H | 3,5-Cl$_2$ | -4-C(O)OMe; |
| 50 | 1 | Pr | H | H | 3-Cl | -4-C(O)OMe; |
| 51 | 1 | Allyl | 2-Me | 5-Me | — | -4-C(O)OMe; |
| 52 | 1 | Allyl | H | H | 2-Cl | -3-C(O)N(Et)$_2$; |
| 53 | 1 | Allyl | H | H | — | -3-C(O)N(Et)$_2$; |
| 54 | 1 | Allyl | H | H | 2-Cl | -3-C(O)OMe; |
| 55 | 1 | Allyl | H | H | — | -3-C(O)OMe; |
| 56 | 2 | Phenethyl | H | H | — | -4-C(O)N(Et)$_2$; |
| 57 | 2 | Phenethyl | H | H | 2-Cl | -4-C(O)N(Et)$_2$; |
| 58 or, | 2 | Phenethyl | H | H | — | -4-C(O)OMe; |
| 59 | 2 | Phenethyl | H | H | 2-Cl | -4-C(O)OMe; | and pharmaceutically acceptable enantiomers, diastereomers and salts thereof.

Instant compounds of the invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharic or trifluoroacetic.

Where the compounds according to this invention are chiral, they may accordingly exist as enantiomers. In addition, the compounds may exist as diastereomers. It is to be understood that all such stereoisomers and racemic mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

The term "alkyl" refers to straight and branched-chain alkyl radical groups and the term "alkylene" refers to a corresponding straight and branched-chain alkyl linking group. Similarly, the "alkenyl" and "alkynyl" refers to radical groups having straight and branched chains with 2 to 8 carbon atoms or any number within this range, wherein one or two double bonds or one triple bond is formed in the chain between adjacent members. The term "alkoxy" refers to O-alkyl groups where alkyl is as defined supra. The term cycloalkyl refers to a cyclic alkyl ring of five to seven carbon atom members. Examples of such cyclic alkyl rings include pentyl, hexyl or heptyl.

The term aryl refers to a single aromatic ring of six carbon members or a bicyclic aromatic ring of ten carbon members. Examples of such aryl rings include phenyl and naphthyl.

The term heteroaryl refers to an aromatic ring of five or six members wherein the ring has at least one heteroatom member. Suitable heteroatoms include nitrogen, oxygen or sulfur. In the case of five-membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent.

The terms "$C_{1-6}$alkoxy($C_{1-6}$)alkyl," "aryl($C_{1-6}$)alkyl," "diaryl($C_{1-6}$)alky" or "heteroaryl($C_{1-6}$)alkyl" refer to an alkylene group substituted at the terminal carbon with an alkoxy, aryl, diaryl or heteroaryl group, respectively. Similarly, the term "$C_{1-6}$alkoxycarbonyl refers to a carbonyl linking group substituted with a terminal alkoxy group.

Whenever the term "alkyl" or "aryl" or either of their prefix roots appear in a name of a substituent (e.g., aryl($C_{1-6}$)alkyl) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "halogen" shall include iodine, bromine, chlorine and fluorine.

The novel benzamidine derivative compounds of the present invention are useful δ-opioid receptor modulators. In particular, the instant benzamidine compounds are δ-opioid receptor selective agonists useful as analgesics having reduced side-effects. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches. The utility of the instant compounds as δ-opioid receptor selective agonists can be determined according to the procedures described herein.

Also, the compounds of the present invention are δ-opioid receptor selective antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. The utility of the instant compounds as δ-opioid receptor selective antagonists can be determined by those skilled in the art using established animal models.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier.

The present invention is also embodied by a pharmaceutical composition comprising a combination of a δ-opioid receptor modulator compound of the present invention and a μ-opioid receptor modulator compound having a synergistic analgesic effect. The utility of the instant combination product can be determined by those skilled in the art using established animal models.

Suitable μ-opioid receptor modulator compounds for use in such a combination include, without limitation, the compounds alfentanil, allylprodine, alphaprodine, anileridine, benzyl-morphine, bezitramide, buprenorphine, butorphanol, clonitazene, cyclazocine, desomorphine, dextromoramide, dezocine, diampromide, diamorphone, dihydrocodeine, dihydromorphine, dimenoxadol, dimepheptanol dimethylthiambutene, dioxaphetylbutyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, diastereomers thereof, salts thereof, complexes thereof; and mixtures of any of the foregoing.

The present invention includes a method for treating a disorder modulated by the δ-opioid receptor. An embodiment of the present invention is a method for treating pain modulated by a δ-opioid agonist. Another embodiment is a method for treating immune disorders, inflammation, neurological conditions, psychiatric conditions, drug abuse, alcohol abuse, gastritis, diarrhea, cardiovascular disorders or respiratory disorders modulated by a δ-opioid antagonist.

The present invention therefore provides a method for the use of the instant benzamidine derivatives as δ-opioid receptor modulators in a subject in need thereof which comprises administering any of the compounds as defined herein in a therapeutically effective dose to modulate the δ-opioid receptor. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective dose for use of the instant compounds or a pharmaceutical composition thereof as a δ-opioid receptor selective agonist, δ-opioid receptor selective antagonist or in a combination δ-opioid/μ-opioid receptor modulator product comprises a dose range of from about 0.01 mg to about 12,000 mg, in particular from about 0.1 mg to about 4000 mg or, more particularly from about 1 mg to about 2000 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as δ-opioid receptor modulators is required for a subject in need thereof.

The terms used in describing the invention are commonly used and known to those skilled in the art. As used herein, the following abbreviations have the indicated meanings:

| Cpd | Compound |
| Et | Ethyl |
| h | Hour |
| Me | Methyl |
| MeOH | Methanol |
| min | Minute |
| Ph | Phenyl |
| POCl$_3$ | Phosphorus oxychloride |
| rt | Room temperature |
| SOCl$_2$ | Thionyl chloride |

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme 1 describes the preparation of certain target benzamide derivative compounds of the invention whereby a piperazine Compound 1a underwent a condensation reaction with a benzoyl acid chloride Compound 1b. For Compound 1b, the variable A may be selected from OH or Cl; X may be selected from O or S; and, Z may be selected from OR$_5$. An example of Compound 1b is terephthalic acid monomethyl ester chloride. The condensation reaction was carried out in a base such as aqueous sodium hydroxide to give the amide Compound 1 c.

The amide Compound 1c was then converted to the iminoylchloride Compound 1d by treatment with phosphorus oxychloride. Upon reaction of the iminochloride Compound 1d with a compound Ar(R$_4$)NH$_2$, such as aniline, the amidino ester Compound 1e was formed.

The ester Compound 1e was hydrolyzed with sodium hydroxide to the corresponding carboxylic acid which was then reacted with thionyl chloride to provide an acid chloride intermediate. The acid chloride intermediate was then reacted with a secondary amine such as, but not limited to, diethyl amine to produce the target amide Compound 1f.

The functional groups in the target compounds may be varied as desired by those skilled in the art using either addition reactions in later steps or using various starting materials or reagents. For example, wherein the desired Ar group is naphthalenyl, the synthetic step for producing Compound 1e may be carried out by reacting Compound 1d with a compound of the formula Ar(R$_4$)NH$_2$, wherein Ar is a naphthalenyl group. Other variable substituted and unsubstituted Ar groups known to one skilled in the art may also be used in this step to produce other compounds intended to be within the scope of the present invention. Similarly, the synthetic sequence may be carried out starting with a removable R$_1$ group such as methyl or BOC. At the conclusion of the sequence shown in Scheme 1, the blocking group may be removed and replaced with the desired R$_1$ substituent.

Scheme 1 illustrates the method described above.

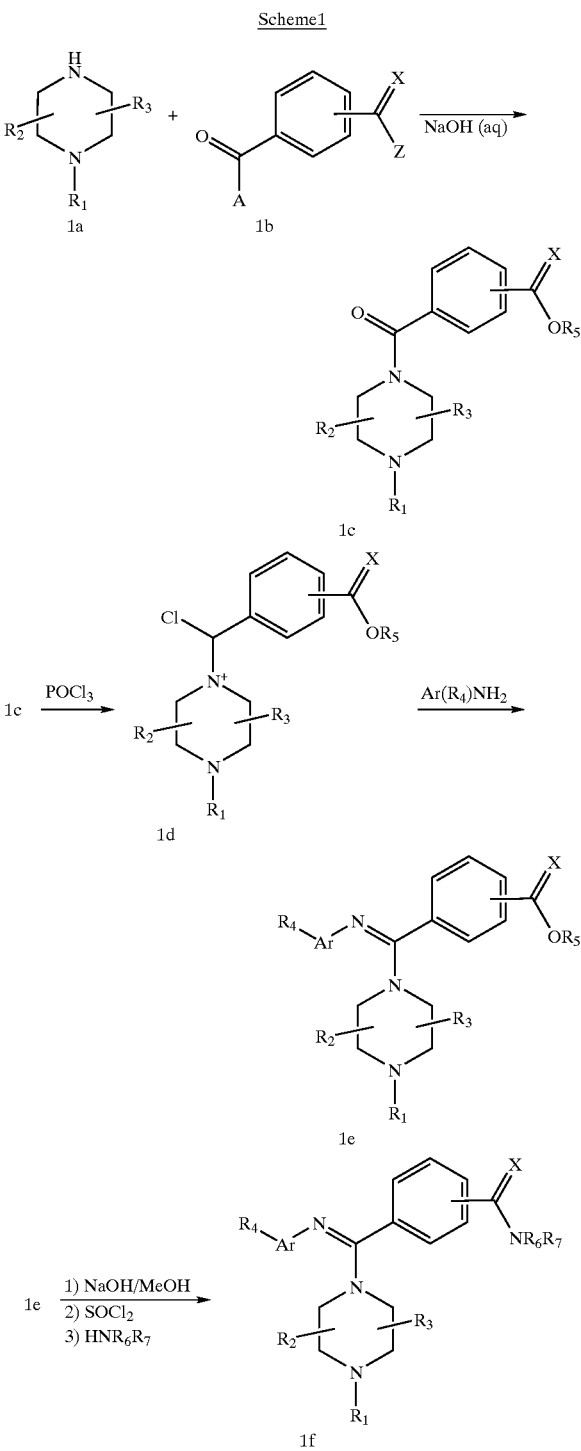

Scheme 2 illustrates the use of Weinreb's method to prepare other target benzamide derivative compounds of the invention; wherein a secondary amine HNR$_6$R$_7$ compound was activated with trimethylaluminum and reacted with ester Compound 1e to directly give the target amide Compound 1f.

Scheme 2

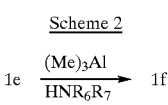

Scheme 3 illustrates a method whereby, in those cases where a particular $R_5$ group may not be amenable to the reactions described in Scheme 1, the $R_5$ group may be interchanged to produce other target benzoic acid alkyl ester derivative compounds of the invention.

In Scheme 3, the ester Compound 1e was converted to another alkyl ester Compound 2a (wherein the $R_5$ ester group may be further varied as desired) by hydrolysis of the ester Compound 1e with sodium hydroxide to the corresponding carboxylic acid. The carboxylic acid was reacted with thionyl chloride to provide an acid chloride intermediate which was then reacted with an alkyl alcohol Compound $HOR_5$ to give the respective target Compound 2a.

Scheme 3

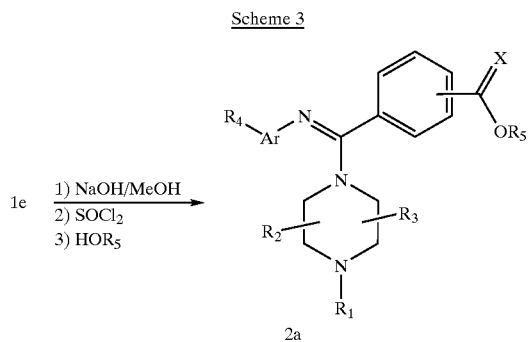

Specific Synthetic Methods

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents.

EXAMPLE 1

4-[[(2-chlorophenyl)imino][4-(phenylmethyl)-1-piperazinyl]methyl]-N,N-diethyl-benzamide (Compound 20)

A solution of 1-benzyl piperazine (8.8 g, 0.05 mol) in dichloromethane (80 mL) was treated with sodium hydroxide solution (1N, 80 mL) and stirred for 15 min and was then treated with a solution of terephthalic acid monomethyl ester chloride (10 g, 0.05 mol) in dichloromethane (20 mL). The mixture was stirred for 24 h, the organic layer was separated, washed with brine, dried ($Na_2SO_4$) and concentrated in vacuo to give an amide ester as a light yellow solid (17.7 g, 98% yield).

The amide ester (4.0 g, 0.012 mol) was dissolved in phosphorus oxychloride (22.14 g, 0.14 mol) and water (0.51 mL) was added cautiously. The mixture was stirred for 5 min, and treated dropwise with 2-chloroaniline (1.66 g, 0.013 mol). The resultant yellow solution was stirred at 80° C. for 24 h. The mixture was concentrated in vacuo, treated with cold water and 3N NaOH was added to pH 10 and extracted twice into dichloromethane. The combined organic extracts were washed with brine, dried ($Na_2SO_4$) and concentrated in vacuo to give an amidine ester (4.0 g) as a syrup, which was used in the next step without further purification.

A solution of the amidine ester (3.6 g, 8.0 mmol) in 3N NaOH (12 mL), and methanol (6 mL) was stirred at 80° C. for 24 h, cooled and neutralized with 3N HCl to about pH 7 to give the respective carboxylate as a pale yellow solid. The carboxylate was dissolved in benzene (30 mL), treated with thionyl chloride (5.5 mL) and refluxed for 3 h. The mixture was concentrated in vacuo to give the crude acid chloride which was immediately dissolved in dichloromethane (12 mL), treated with 1N NaOH (12 mL) and cooled. A solution of diethylamine (8 mL) in dichloromethane (4 mL) was added at 0–5° C. After addition, the mixture was stirred at room temperature for 18 h. The organic layer was washed with brine, dried ($Na_2SO_4$) and concentrated in vacuo. The residue was purified on a prep-500 HPLC using ethyl acetate:hexane:methanol (8:2:1) as eluents to give Compound 20 as a syrup (1.20 g). A representative sample was converted to the oxalate salt in 2-propanol and recrystallized in the same solvent to give a pure sample. MS m/z 489($M^+$); 491($M^{+2}$). 300 MHz $^1H$ NMR ($CDCl_3$) δ 7.08–7.32 (m, 10H); 6.8 (t, 1H); 6.60 (t, 1H); 6.40 (d, 1H); 3.55 (s, 2H); 3.35–3.50 (m, 6H); 2.80–3.05 (m, 2H); 2.35–2.06 (m, 4H); 1.10–1.25 (m, 3H); 0.88–1.05 (m, 3H); Anal calcd. for $C_{29}H_{33}ClN_4O\cdot C_2H_2O_4\cdot 0.2H_2O$: C, 63.90; H, 6.12; Cl, 6.08; N, 9.61. Found: C, 63.55; H, 5.90; Cl, 6.47; N, 9.34.

EXAMPLE 2

Following the procedure of Example 1 and substituting the appropriate starting materials, reagents and solvents the following compounds were prepared:

| Ex# | MS m/z ($M^+$) | MS m/z ($M^{+2}$) |
|---|---|---|
| 15 | 405 | — |
| 16 | 433 | — |
| 17 | 455 | — |
| 18 | 439 | 441 |
| 19 | 439 | 441 |
| 21 | 509 | 511 |
| 22 | 475 | — |
| 23 | 523 | — |
| 24 | 537 | — |
| 25 | 503 | 505 |
| 26 | 491 | — |
| 27 | 457 | 459 |
| 28 | 489 | 491 |
| 52 | 439 | 441 |
| 53 | 405 | — |
| 54 | 397 | 399 |
| 55 | 439 | 441 |
| 56 | 483 | — |
| 57 | 517 | 519 |
| 58 | 442 | — |
| 59 | 475 | 477 |

EXAMPLE 3

4-[[(3-chlorophenyl)imino](4-propyl-1-piperazinyl)methyl]-N,N-diethyl-benzamide (Compound 14)

A mixture of trimethylaluminum (2M/toluene, 2.41 mL, 4.8 mmol), diethylamine (0.51 mL, 4.8 mmol) in dichloromethane (9 mL) was stirred for 4 h at room temperature and treated with a solution of a 3-chloro amidine ester derivative (prepared as in Example 1, 0.55 g, 1.4 mmol) in dichloromethane and heated to 45° C. for 28 h. The mixture was poured over ice, treated with 1N HCl (pH 1) and washed with dichloromethane. The aqueous layer was neutralized with 3N NaOH and extracted with dichloromethane twice. The combined organic extracts were dried ($Na_2SO_4$) and concentrated in vacuo. The residue was purified by preparative TLC (5×1000 micron plates; EtOAc:Hexane:MeOH:$CH_2Cl_2$:$NH_4OH$; 10:5:1:1:0.1) to give Compound 14 as a syrup. MS m/z 441($M^+$); 443($M^{+2}$). MS m/z=441 ($M^+$+H). 300 MHz $^1$H NMR ($CDCl_3$) δ7.18–7.20 (m, 2H); 7.05–7.15 (m, 2H); 6.85–6.92 (m, 1H); 6.60–6.69 (m, 1H); 6.40–6.48 (m, 1H); 6.39 (s, 1H); 3.22–3.8 (m, 6H); 2.95–3.10 (m, 2H); 2.40–2.60 (m, 1H); 2.30–2.39 (t, 2H); 1.45–1.60 (m, 2H); 1.10–1.25 (m, 3H); 0.95–1.05 (M, 3H); 0.85–0.94 (t, 3H).

EXAMPLE 4

Following the procedure of Example 3 and substituting the appropriate starting materials, reagents and solvents the following compounds were prepared:

| Ex# | MS m/z (MH+) | MS m/z ($MH^{+2}$) |
| --- | --- | --- |
| 1 | 393 | — |
| 2 | 423 | — |
| 3 | 427 | 429 |
| 4 | 472 | — |
| 5 | 500 | — |
| 6 | 427 | 429 |
| 7 | 455 | 457 |
| 8 | 439 | — |
| 9 | 411 | — |
| 10 | 411 | — |
| 11 | 439 | — |
| 12 | 490 | — |
| 13 | 462 | — |

EXAMPLE 5

4-[[(2-chlorophenyl)imino][4-(phenylmethyl)-1-piperazinyl]methyl]-benzoic Acid Methyl Ester; (Compound 39)

A solution of 1-benzyl piperazine (8.8 g, 0.05 mol) in dichloromethane (80 mL) was treated with sodium hydroxide solution (1N, 80 mL) and stirred for 15 min and was then treated with a solution of terephthalic acid monomethyl ester chloride (10 g, 0.05 mol) in dichloromethane (20 mL). The mixture was stirred for 24 h, the organic layer was separated, washed with brine, dried ($Na_2SO_4$) and concentrated in vacuo to give an amide ester as a light yellow solid (17.7 g, 98% yield).

The amide ester (4.0 g, 0.012 mol) was dissolved in phosphorus oxychloride (22.14 g, 0.14 mol) and water (0.51 mL) was added cautiously. The mixture was stirred for 5 min, and treated dropwise with 2-chloroaniline (1.66 g, 0.013 mol). The resultant yellow solution was stirred at 80° C. for 24 h. The mixture was concentrated in vacuo, treated with cold water and 3N NaOH was added to pH 10 and extracted twice into dichloromethane. The combined organic extracts were washed with brine, dried ($Na_2SO_4$) and concentrated in vacuo to give the amidine ester Compound 39 (4.0 g) as a syrup. MS m/z 447($M^+$); 447($M^+$).

EXAMPLE 6

Following the procedure of Example 5 and substituting the appropriate starting materials, reagents and solvents the following compounds were prepared:

| Ex# | MS m/z ($MH^+$) | MS m/z ($MH^{+2}$) |
| --- | --- | --- |
| 29 | 385 | 387 |
| 30 | 431 | — |
| 31 | 385 | 387 |
| 32 | 370 | — |
| 33 | 370 | — |
| 34 | 399 | 401 |
| 35 | 433 | 435 |
| 36 | 364 | — |
| 37 | 414 | — |
| 38 | 447 | 449 |
| 40 | 461 | 463 |
| 41 | 496 | — |
| 42 | 434 | — |
| 43 | 467 | 469 |
| 44 | 450 | — |
| 45 | 415 | 417 |
| 46 | 352 | — |
| 47 | 382 | — |
| 48 | 382 | — |
| 49 | 419 | 421 |
| 50 | 399 | 401 |
| 51 | 392 | — |

Biological Examples

δ-opioid and μ-opioid receptor binding for the compounds of the present invention were determined according to the following procedures and the indicated results were obtained.

Scintillation Screening Assay for δ-Opioid Receptor Binding

This is a receptor based screen to detect the competitive binding of test compounds at the δ-opioid receptor against the radioligand, [$^3$H]bremazocine (S.A.=25.5 Cl/mmol, Dupont/NEN, Cambridge, Mass.). Unknown compounds that bind to the same receptor as the radioligand will compete for the receptor and reduce the amount of radioligand which binds to the receptor. This is detected as a decreased scintillation signal from that particular incubation. The greater affinity an unknown has for the receptor, the larger the observed decrease in radioligand bound radioligand bound to the receptor; thus the assay is in the format of an inhibition study.

Materials

The receptor is a cloned human cDNA expressed in mammalian CHO cells. Membranes prepared from these cells are purchased from Receptor Biology, Baltimore, Md. The reaction buffer is composed as follows: HEPES (50 mM final), MgCl.$6H_2O$ (5 mM final), o-phenanthroline (20 mg/l), aprotinin (10 mg/l), Pefabloc SC (250 mg/l), leupeptin (0.5 mg/l), pepstatin A (0.7 mg/l), trypsin inhibitor (25 mg/l), chymostatin (10 mg/l), pH=7.2. Naloxone, 10 uM, is used to define non-specific binding. The assay employs filtration to capture receptor and bound ligand.

Procedure

The receptor (membrane) preparation (28 ug protein) is allowed to incubate with the opioid receptor radioligand ([$^3$H]bremazocine, 2.4 nM) in 96-well plates until equilibrium is reached (>2 hr). Following incubation with the radioligand at 23° C., the well contents are filtered onto 96-well Whatman GF/C filter plates using a Packard cell harvester. Radioligand bound to the receptor also remains on the filter. The filters are rinsed three times with 0.5 mL of physiological saline (0.9% NaCl) to remove any unbound radioligand from the filter. Filters are dried and scintillation fluid is then added to the filters which emits light in proportion to the amount of radioactivity on the filter which is determined using an Packard Topcount scintillation counter. Data are reported as percent inhibition of control binding.

Results

Table 3 shows the biological activity in % inhibition for 25 μM solutions for a number of the instant compounds in the scintillation assay for δ-opioid receptor binding.

TABLE 3

δ-Opioid Receptor Binding (% Inhibition)

| Cpd | % I @ 25 μM |
|---|---|
| 1 | 106 |
| 3 | 103 |
| 4 | 100 |
| 5 | 100 |
| 6 | 103 |
| 7 | 97 |
| 8 | 97 |
| 9 | 97 |
| 10 | 102 |
| 11 | 98 |
| 12 | 98 |
| 13 | 100 |
| 14 | 101 |
| 29 | 97 |
| 30 | 99 |
| 31 | 100 |
| 32 | 97 |
| 33 | 100 |
| 34 | 90 |
| 46 | 94 |
| 47 | 91 |
| 48 | 60 |

Manual Tissue Screening Assay for δ- and μ-Opioid Receptor Binding Rat Brain δ-Opioid Receptor Binding Assay The activity of the compounds of the invention as analgesics was demonstrated by the rat brain δ-opioid receptor binding assay as described below.

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [³H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations are tested). % Inhibition was calculated as:

$$1 - \left(\frac{\text{test compound } dpm - \text{nonspecific } dpm}{\text{total } dpm - \text{nonspecific } dpm}\right) \times 100\%;$$

$K_i$ value is calculated using the LIGAND (Munson, P. J. and Rodbard, D., Anal. Biochem. 107: 220–239, 1980) data analysis program. Those compounds with $K_i$ values of >10000 nM are considered to be biologically inactive.

Table 4 shows the biological activity in % inhibition for instant compounds as measured in the rat brain δ-opioid receptor binding assay.

TABLE 4

δ-Opioid Receptor Binding ($K_i$ nM)

| Cpd | $K_i$ nM |
|---|---|
| 1 | 16 |
| 3 | 62.6 |
| 4 | 57.6 |
| 5 | 39.2 |
| 6 | 91.1 |
| 7 | 291.8 |
| 8 | 60.7 |
| 9 | 58.5 |
| 10 | 118 |
| 11 | 256 |
| 12 | 674.5 |
| 13 | 277.3 |
| 14 | 176.8 |
| 15 | 859 |
| 16 | 170 |
| 17 | 212 |
| 18 | 157.4 |
| 19 | 20.5 |
| 20 | 11.8 |
| 21 | 95.3 |
| 22 | 764 |
| 23 | 1.22 |
| 24 | 545 |
| 25 | >10000 |
| 26 | 22.9 |
| 27 | 53.5 |
| 28 | 142 |
| 29 | 283 |
| 30 | 638.3 |
| 31 | 221.6 |
| 32 | 259 |
| 33 | 230 |
| 34 | 87.3 |
| 35 | 7640 |
| 36 | 954 |
| 37 | 1690 |
| 38 | 246 |
| 39 | 2010 |
| 40 | >10000 |
| 41 | >10000 |
| 42 | >10000 |
| 43 | >10000 |

TABLE 4-continued

δ-Opioid Receptor Binding ($K_i$ nM)

| Cpd | $K_i$ nM |
|---|---|
| 44 | 82.6 |
| 45 | 299 |
| 51 | 405 |
| 52 | 487 |
| 53 | 7030 |
| 54 | 2149 |
| 55 | 1173 |
| 56 | 396 |
| 57 | 29.6 |
| 58 | 820 |
| 59 | 101 |

Rat Brain μ-Opioid Receptor Binding Assay

The activity of compounds of the invention as analgesics is demonstrated by the rat brain μ-opioid receptor binding assay as described below.

Procedure

Male, Wistar rats (150–250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the μ-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested). % Inhibition is calculated as:

$$1 - \left(\frac{\text{test compound } dpm - \text{nonspecific } dpm}{\text{total } dpm - \text{nonspecific } dpm}\right) \times 100\%;$$

$K_i$ value is calculated using the LIGAND (Munson, P. J. and Rodbard, D., Anal. Biochem. 107: 220–239, 1980) data analysis program. Those compounds with $K_i$ values of >10000 nM are considered to be biologically inactive.

Table 5 shows the biological activity in % inhibition for instant compounds as measured in the rat brain μ-opioid receptor binding assay.

TABLE 5

μ-Opioid Receptor Binding ($K_i$ nM)

| Cpd | $K_i$ nM |
|---|---|
| 1 | >10000 |
| 3 | >10000 |
| 4 | >10000 |
| 5 | 5510 |
| 6 | >10000 |
| 7 | 3930 |
| 8 | 6890 |
| 9 | >10000 |
| 10 | >10000 |
| 11 | >10000 |
| 12 | >10000 |
| 13 | >10000 |
| 14 | 9530 |
| 15 | >10000 |
| 16 | 4330 |
| 17 | >10000 |
| 18 | >10000 |
| 19 | 7600 |
| 20 | >10000 |
| 21 | >10000 |
| 22 | >10000 |
| 23 | 1200 |
| 24 | 1000 |
| 25 | >10000 |
| 26 | 2960 |
| 27 | >10000 |
| 28 | >10000 |
| 29 | >10000 |
| 30 | >10000 |
| 31 | >10000 |
| 32 | >10000 |
| 33 | >10000 |
| 34 | 2070 |
| 35 | >10000 |
| 36 | >10000 |
| 37 | >10000 |
| 38 | >10000 |
| 39 | >10000 |
| 40 | >10000 |
| 41 | >10000 |
| 42 | >10000 |
| 43 | >10000 |
| 44 | 9150 |
| 45 | >10000 |
| 51 | >10000 |
| 52 | 600 |
| 53 | >10000 |
| 54 | 1610 |
| 55 | >10000 |
| 57 | 618 |
| 58 | 232 |
| 59 | 197 |

Mouse Acetylcholine Bromide-Induced Abdominal Constriction Assay

The activity of compounds of the invention as analgesics was further demonstrated by the mouse acetylcholine bromide-induced abdominal constriction assay as described below.

Procedure

The mouse acetylcholine-induced abdominal constriction assay, as described by Collier et al. in *Bit. J. Pharmacol. Chem. Ther.*, 32: 295–310, 1968 with minor modifications, was used to assess analgesic potency of the compounds of formula (I). The test drugs or appropriate vehicles were administered orally (p.o.) and 30 min later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten min observation period for the occurrence of an abdominal constriction response (defined as a wave of constriction and elongation passing caudally along the abdominal wall, accompanied by a twisting of the trunk and followed by extension of the hind limbs). For compounds of the present invention, the percent inhibition of this response to a nociceptive stimulus (equated to % analgesia) was calculated as follows:

% Inhibition of response (i.e., % analgesia) =

$$\left(\frac{\text{No. of } CAR - \text{No. of } DTAR}{\text{No. of } CAR}\right) \times 100\%$$

Table 6 shows the biological activity in % inhibition at a dose of 150 μmole/Kg p.o. for instant compounds as measured in the mouse acetylcholine bromide-induced abdominal constriction (MAIT) assay.

TABLE 6

MAIT (% Inhibition)

| Cpd | % Inhibition |
|-----|--------------|
| 1   | 40           |
| 3   | 40           |
| 4   | 7.7          |
| 5   | 14.3         |
| 6   | 20           |
| 8   | 7.1          |
| 10  | 26.7         |
| 16  | 50           |
| 19  | 40           |
| 20  | 23.1         |
| 21  | 40           |
| 46  | 26.7         |
| 47  | 26.7         |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

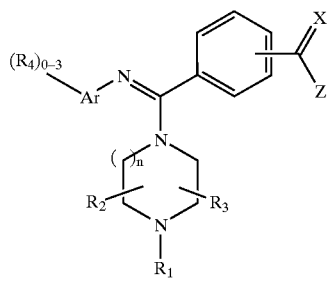

Formula (I)

wherein:
R$_1$ is a substituent selected from the group consisting of hydrogen, C$_{1-6}$alkyl, C$_{1-6}$alkoxy(C$_{1-6}$)alkyl, allyl, phenyl, phenyl(C$_{1-6}$)alkyl, and thienyl(C$_{1-6}$)alkyl;
R$_2$ and R$_3$ are substituents independently selected from the group consisting of hydrogen and C$_{1-6}$alkyl;
R$_4$ is either one or two substituents independently selected from the group consisting of halogen, C$_{1-6}$alkoxy, and trihaloC$_{1-4}$alkyl;

X is a substituent selected from the group consisting of O(R$_5$) and N(R$_6$)(R$_7$); wherein
R$_5$ is a substituent selected from C$_{1-6}$alkyl; and,
R$_6$ and R$_7$ are substituents independently selected from the group consisting of hydrogen and C$_{1-6}$alkyl;
and n is the integer 1;
and pharmaceutically acceptable enantiomers, diastereomers and salts thereof.

2. The compound of claim 1 wherein R$_1$ is a substituent selected from the group consisting of hydrogen, methyl, ethyl, n-propyl, n-butyl, n-hexyl, allyl, methoxy(C$_{1-3}$)alkyl, ethoxy(C$_{1-3}$)alkyl, propoxy(C$_{1-3}$)alkyl, phenyl(C$_{2-3}$)alkyl, and thienyl(C$_{1-3}$)alkyl.

3. The compound of claim 2 wherein R$_1$ is a substituent selected from the group consisting of hydrogen, ethyl, n-propyl, allyl, methoxyethyl, phenyl, benzyl, phenethyl and 2-thienylethyl.

4. The compound of claim 1 wherein R$_2$ and R$_3$ are substituents independently selected from the group consisting of hydrogen, methyl, ethyl, n-propyl and n-butyl.

5. The compound of claim 1 wherein R$_2$ and R$_3$ are substituents independently selected from the group consisting of hydrogen and methyl.

6. The compound of claim 1 wherein R$_4$ is a substituent selected from the group consisting of chlorine, fluorine, bromine, methoxy, ethoxy, propoxy, butoxy, trifluoromethyl and trifluoroethyl.

7. The compound of claim 6 wherein R$_4$ is a substituent selected from the group consisting of chlorine, fluorine, bromine, methoxy and trifluoromethyl.

8. The compound of claim 6 wherein R$_4$ is two substituents which are chlorine.

9. The compound of claim 1 wherein R$_5$ is a substituent selected from the group consisting of methyl, ethyl, n-propyl and n-butyl.

10. The compound of claim 9 wherein R$_5$ is methyl.

11. The compound of claim 1 wherein R$_6$ and R$_7$ are substituents independently selected from the group consisting of hydrogen, methyl, ethyl, n-propyl and n-butyl.

12. The compound of claim 11 wherein R$_6$ and R$_7$ are substituents independently selected from the group consisting of ethyl and n-propyl.

13. The compound of claim 1 of the formula:

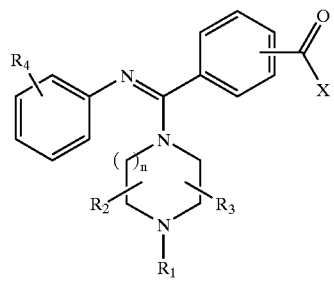

wherein n, R$_1$, R$_2$, R$_3$, R$_4$ and X are selected from the group consisting of:

| n | R$_1$ | R$_2$ | R$_3$ | R$_4$ | —C(O)X |
|---|-------|-------|-------|-------|--------|
| 1 | Et    | H     | H     | —     | -4-C(O)N(Et)$_2$; |
| 1 | Et    | H     | H     | 3-MeO | -4-C(O)N(Et)$_2$; |
| 1 | Et    | H     | H     | 3-Cl  | -4-C(O)N(Et)$_2$; |
| 1 | Et    | H     | H     | 3-Br  | -4-C(O)N(Et)$_2$; |
| 1 | Et    | H     | H     | 3-Br  | -4-C(O)N(Pr)$_2$; |
| 1 | Et    | H     | H     | 2-Cl  | -4-C(O)N(Et)$_2$; |
| 1 | Et    | H     | H     | 2-Cl  | -4-C(O)N(Pr)$_2$; |

-continued

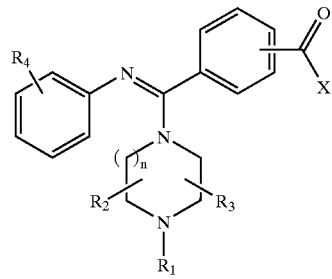

wherein n, R₁, R₂, R₃, R₄ and X are selected from the group consisting of:

| n | R₁ | R₂ | R₃ | R₄ | —C(O)X |
|---|---|---|---|---|---|
| 1 | Et | H | H | 3-F | -4-C(O)N(Pr)₂; |
| 1 | Et | H | H | 3-F | -4-C(O)N(Et)₂; |
| 1 | Et | H | H | 2-F | -4-C(O)N(Et)₂; |
| 1 | Et | H | H | 2-F | -4-C(O)N(Pr)₂; |
| 1 | Et | H | H | 3,5-Cl₂ | -4-C(O)N(Pr)₂; |
| 1 | Et | H | H | 3,5-Cl₂ | -4-C(O)N(Et)₂; |
| 1 | Pr | H | H | 3-Cl | -4-C(O)N(Et)₂; |
| 1 | Allyl | H | H | — | -4-C(O)N(Et)₂; |
| 1 | Allyl | 2-Me | 5-Me | — | -4-C(O)N(Et)₂; |
| 1 | Benzyl | H | H | — | -4-C(O)N(Et)₂; |
| 1 | Allyl | H | H | 3-Cl | -4-C(O)N(Et)₂; |
| 1 | Allyl | H | H | 2-Cl | -4-C(O)N(Et)₂; |
| 1 | Benzyl | H | H | 2-Cl | -4-C(O)N(Et)₂; |
| 1 | 2-(2-thienyl)ethyl | H | H | 2-Cl | -4-C(O)N(Et)₂; |
| 1 | 2-(2-thienyl)ethyl | H | H | — | -4-C(O)N(Et)₂; |
| 1 | Benzyl | H | H | 2-CF₃ | -4-C(O)N(Et)₂; |
| 1 | Phenethyl | H | H | 2-CF₃ | -4-C(O)N(Et)₂; |
| 1 | Phenethyl | H | H | 2-Cl | -4-C(O)N(Et)₂; |
| 1 | 2-(methoxy)ethyl | H | H | 2-CF₃ | -4-C(O)N(Et)₂; |
| 1 | 2-(methoxy)ethyl | H | H | 2-Cl | -4-C(O)N(Et)₂; |
| 1 | Benzyl | H | H | 4-Cl | -4-C(O)N(Et)₂; |
| 1 | Et | H | H | 3-Cl | -4-C(O)OMe; |
| 1 | Et | H | H | 3-Br | -4-C(O)OMe; |
| 1 | Et | H | H | 2-Cl | -4-C(O)OMe; |
| 1 | Et | H | H | 3-F | -4-C(O)OMe; |
| 1 | Et | H | H | 2-F | -4-C(O)OMe; |
| 1 | Pr | H | H | 2-Cl | -4-C(O)OMe; |
| 1 | Ph | H | H | 2-Cl | -4-C(O)OMe; |
| 1 | Allyl | H | H | — | -4-C(O)OMe; |
| 1 | Benzyl | H | H | — | -4-C(O)OMe; |
| 1 | Benzyl | H | H | 4-Cl | -4-C(O)OMe; |
| 1 | Benzyl | H | H | 2-Cl | -4-C(O)OMe; |
| 1 | Phenethyl | H | H | 2-Cl | -4-C(O)OMe; |
| 1 | Phenethyl | H | H | 2-CF₃ | -4-C(O)OMe; |

-continued

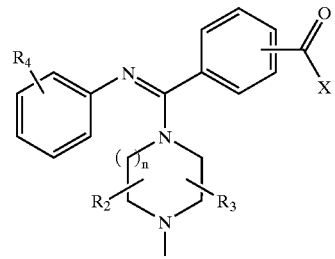

wherein n, R₁, R₂, R₃, R₄ and X are selected from the group consisting of:

| n | R₁ | R₂ | R₃ | R₄ | —C(O)X |
|---|---|---|---|---|---|
| 1 | 2-(2-thienyl)ethyl | H | H | — | -4-C(O)OMe; |
| 1 | 2-(2-thienyl)ethyl | H | H | 2-Cl | -4-C(O)OMe; |
| 1 | 2-(methoxy)ethyl | H | H | 2-CF3 | -4-C(O)OMe; |
| 1 | 2-(methoxy)ethyl | H | H | 2-Cl | -4-C(O)OMe; |
| 1 | Et | H | H | — | -4-C(O)OMe; |
| 1 | Et | H | H | 3-MeO | -4-C(O)OMe; |
| 1 | Et | H | H | 2-MeO | -4-C(O)OMe; |
| 1 | Et | H | H | 3,5-Cl₂ | -4-C(O)OMe; |
| 1 | Pr | H | H | 3-Cl | -4-C(O)OMe; |
| 1 | Allyl | 2-Me | 5-Me | — | -4-C(O)OMe; |
| 1 | Allyl | H | H | 2-Cl | -3-C(O)N(Et)₂; |
| 1 | Allyl | H | H | — | -3-C(O)N(Et)₂; |
| 1 | Allyl | H | H | 2-Cl | -3-C(O)OMe; |
| 1 | Allyl | H | H | — | -3-C(O)OMe; |
| 2 | Phenethyl | H | H | — | -4-C(O)N(Et)₂; |
| 2 | Phenethyl | H | H | 2-Cl | -4-C(O)N(Et)₂; |
| 2 | Phenethyl | H | H | — | -4-C(O)OMe; |
| 2 | Phenethyl | H | H | 2-Cl | -4-C(O)OMe; | and pharmaceutically acceptable enantiomers, diastereomers and salts thereof.

14. A pharmaceutical composition comprising a compound of claim 1, and pharmaceutically acceptable enantiomers, diastereomers and salts thereof and a pharmaceutically acceptable carrier.

15. A method for treating pain in a subject in need thereof comprising administering to the subject a therapeutically effective amount of a compound of claim 1.

\* \* \* \* \*